United States Patent
Chang et al.

(10) Patent No.: US 8,258,135 B2
(45) Date of Patent: Sep. 4, 2012

(54) QUINOLIZIDINONE M1 RECEPTOR POSITIVE ALLOSTERIC MODULATORS

(75) Inventors: Ronald K. Chang, Oreland, PA (US); Scott D. Kuduk, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 309 days.

(21) Appl. No.: 12/738,208

(22) PCT Filed: Oct. 15, 2008

(86) PCT No.: PCT/US2008/011752
§ 371 (c)(1),
(2), (4) Date: Apr. 15, 2010

(87) PCT Pub. No.: WO2009/051715
PCT Pub. Date: Apr. 23, 2009

(65) Prior Publication Data
US 2010/0222355 A1    Sep. 2, 2010

Related U.S. Application Data

(60) Provisional application No. 60/999,424, filed on Oct. 18, 2007.

(51) Int. Cl.
*A61K 31/498* (2006.01)
*A61K 31/4545* (2006.01)
*C07D 455/02* (2006.01)
*C07D 241/42* (2006.01)
*A61P 25/00* (2006.01)
*A61P 29/00* (2006.01)

(52) U.S. Cl. ......... 514/249; 546/138; 544/353; 514/306

(58) Field of Classification Search ................. 546/138; 514/306, 249; 544/353
See application file for complete search history.

(56) References Cited

U.S. PATENT DOCUMENTS
6,030,984 A    2/2000    Trottman et al.
2010/0324024 A1*  12/2010  Kuduk et al. ................. 514/215

FOREIGN PATENT DOCUMENTS
WO    9825930    2/2004
WO    2006033422    3/2006

OTHER PUBLICATIONS

Potter et al., Investigational medications for Alzheimer disease, vol. 110(9), 2010, pp. 527-536.*
N. J. M Birdsall et al., "Multiple Allosteric Sites on Muscarinic Receptors", vol. 68, pp. 2517-2524, Life Sciences, 2001.
M.P. Caulfield, "Muscarnic Receptors—Characterization, Coupling and Function", vol. 58, pp. 319-379, Pharmac. Ther., 1993.
R. M. Eglen et al., "Therapeutic Opportunities from Muscarinic Receptor Research", vol. 22, pp. 409-414, Trends, 2001.
A. Fisher, "Therapeutic Strategies in Alzheimer's Disease: M1 Muscarinic Agonists", vol. 84, pp. 101-112, Jpn. J. Pharmacol., 2000.
S. Lazareno et al., "Allosteric Interactions of Staurosporine and Other Indolocarbazoles with N-[methyl-3H] Scopolamine and Acetycholine at Muscarinic Receptor Subtypes: Identification of a Second Allosteric Site", vol. 58, pp. 194-207, The American Society for Pharmacology and Experimental Therapeutics.
T. A. Spalding et al., "Discovery of an Ectopic Activation Site on the M1 Muscarinic Receptor", vol. 61, pp. 1297-1302, Molecular Pharmacology, 2002.
S. Lazareno et al., "Analogs of WIN 62,577 Define a Second Allosteric Site on Muscarinic Receptors", vol. 62, pp. 1492-1505, 2002.
A. Christopoulos et al, "Allosteric Binding Sites on Cell-Surface Receptors: Novel Targets for Drug Discovery", vol. 1, pp. 198-210, Nature.
H. Brauner-Osborne et al., "Pharmacology of Muscarinic Acetylcholine Receptor Subtypes (m1-m5): High Throughput Assays in Mammalian Cells", vol. 295, pp. 93-102, E. J. of Pharmacology., 1996.
H. Komatsu et al., "Design and Synthesis of Highly Sensitive and Selective Fluroescein-Derived Magnesium Fluorescent Probes and Application to Intracelluar 3D Mg2+ Imaging", vol. 126, pp. 16353-16360, 2004.

* cited by examiner

*Primary Examiner* — Niloofar Rahmani
(74) *Attorney, Agent, or Firm* — Sylvia A. Ayler; Gerard M. Devlin

(57) ABSTRACT

The present invention is directed to spiropiperidine compounds of formula (I) which are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

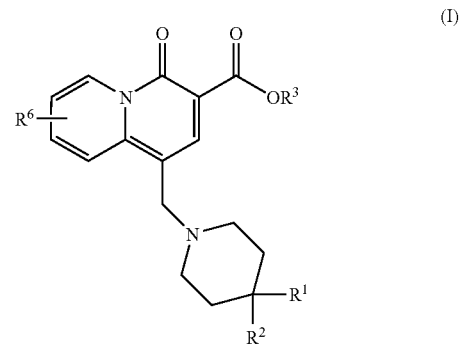

16 Claims, No Drawings

QUINOLIZIDINONE M1 RECEPTOR POSITIVE ALLOSTERIC MODULATORS

CROSS REFERENCE TO RELATED APPLICATIONS

This application is the National Stage of International Application No. PCT/US2008/011752 filed on Oct. 15, 2008, which claims the benefit under 35 U.S.C. 119(e) of U.S. Provisional Applications No. 60/999,424 filed Oct. 18, 2007.

FIELD OF THE INVENTION

The invention is directed to a class of quinolizidinone compounds, their salts, pharmaceutical compositions comprising them and their use in therapy of the human body. In particular, the invention is directed to a class of quinolizidinone compounds which are muscarinic M1 receptor positive allosteric modulators, and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, *TRENDS in Pharmacological Sciences*, 2001, 22:8, 409-414. In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, *Jpn J Pharmacol*, 2000, 84:101-112.

However, M1 ligands which have been developed and studied for Alzheimer's Disease have produced side effects common to other muscarinic receptor ligands, such as sweating, nausea and diarrhea. See Spalding et al, *Mol Pharmacol*, 2002, 61:6, 1297-1302.

The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505; S. Lazareno et al, *Mol Pharmacol*, 2000, 58, 194-207.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is novel compounds generic formula (I)

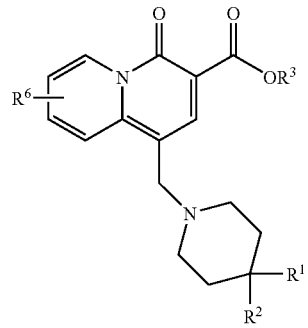

or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula (I)

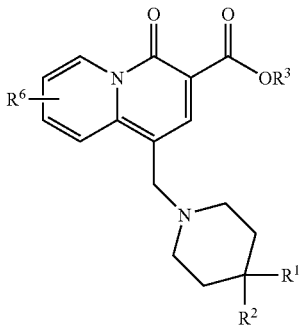

and pharmaceutically acceptable salts thereof, wherein
$R^1$ is selected from the group consisting of
(1) cyano,
(2) —C(=O)—$OR^{4A}$,
(3) —C(=O)—$R^{4A}$,
(4) —OH, and
(5) phenyl;
$R^2$ is selected from the group consisting of
(1) —$(CH_2)_n$-aryl, and
(2) heteroaryl,
wherein said aryl or heteroaryl moiety is optionally substituted with one or more
(a) halogen,
(b) hydroxy,
(c) —O—$C_{1-6}$ alkyl,
(d) —$C_{1-6}$ alkyl,
(e) —$C_{2-6}$ alkenyl
(e) —$S(O)_m$—$R^{4A}$,
(g) —$C_{2-6}$ alkynyl, and
(h) —$N(R^{4A}R^{4B})$;
$R^3$ is selected from the group consisting of
(1) hydrogen,
(2) —$C_{1-6}$ alkyl, and
(3) —$CH_2$-aryl,
wherein said $R^3$ alkyl or aryl moiety is optionally substituted with one or more
(a) halogen,
(b) cyano, and
(c) —O—$C_{1-6}$ alkyl, wherein said alkyl is optionally substituted with one or more halo;
$R^{4A}$ and $R^{4B}$ are independently selected from the group consisting of
(1) hydrogen,
(2) —$C_{1-6}$ alkyl, and
(3) —$(CH_2)_n$-aryl,
wherein said $R^{4A}$ or $R^{4B}$ alkyl or aryl moiety is optionally substituted with one or more
(a) halogen,
(b) cyano, and
(c) —O—$C_{1-6}$ alkyl, wherein said alkyl is optionally substituted with one or more halo;
$R^6$ is optionally present at one or more of the ring carbon atoms, and each $R^6$ is independently selected from the group consisting of
(1) halogen,
(2) —$C_{1-6}$ alkyl, and
(3) —$(CH_2)_n$-aryl, wherein said $R^6$ alkyl or aryl moiety is optionally substituted with one or more
(a) halogen,
(b) cyano, and
(c) —O—$C_{1-6}$ alkyl, wherein said alkyl is optionally substituted with one or more halo;
m is 0, 1 or 2;
n is 0, 1 or 2.

In particular embodiments of the compounds of formula (I), $R^1$ is cyano.

In alternative embodiments of the compounds of formula (I), $R^1$ is selected from the group consisting of
(1) —C(=O)—$OR^{4A}$,
(2) —C(=O)—$R^{4A}$, and
(3) —OH. Exemplary $R^1$ groups in this embodiment include —C(=O)—$CH_3$, phenyl, hydroxy and —C(=O)—$OCH_2CH_3$.

In particular embodiments, $R^{4A}$ and $R^{4B}$ are each independently selected from $C_{1-6}$ alkyl, preferably $C_{1-3}$ alkyl.

In particular embodiments of the compounds of formula (I), $R^2$ is pyridyl, preferably pyridin-2-yl, pyridin-3-yl and pyridin-4-yl. In certain embodiments, the pyridyl group is optionally substituted with one or more
(a) halogen,
(b) hydroxy,
(c) —O—$C_{1-6}$ alkyl
(d) —$C_{1-6}$ alkyl, and
(e) —$C_{2-6}$ alkenyl.

In other embodiments, $R^2$ is another heteroaryl, such as quinoxalinyl (preferably 2-quinoxalinyl), benzoxazolyl (preferably benzoxazol-2-yl), thiazolyl (preferably thiazol-2-yl), and benzothiazolyl (preferably benzothiazol-2-yl). The alternative heteroaryl is optionally substituted with one or more
(a) halogen,
(b) hydroxy,
(c) —O—$C_{1-6}$ alkyl
(d) —$C_{1-6}$ alkyl, and
(e) —$C_{2-6}$ alkenyl.

In alternative embodiments, $R^2$ is phenyl, optionally substituted with one or more
(a) halogen,
(b) hydroxy,
(c) —O—$C_{1-6}$ alkyl
(d) —$C_{1-6}$ alkyl, or
(e) —$C_{2-6}$ alkenyl.

Exemplary $R^2$ groups include 2-pyridyl, 4-fluorophenyl, 2-fluorophenyl, 2,4-difluorophenyl, 4-cyanophenyl, 3-methylphenyl, 2-methoxyphenyl, 3-fluoro-2-pyridiyl, 3-bromo-2-pyridyl, 3-methyl-2-pyridyl, 5-bromo-2-pyridyl, 5-methyl-2-pyridyl, 5-fluoro-2-pyridyl, 5-chloro-2-pyridyl, 5-cyano-2-pyridyl, 5-trifluoromethyl-2-pyridyl, 5-ethyl-2-pyridyl, 5-cyano-2-pyridyl, 5-methoxy-2-pyridyl, 5-sulfido-methyl-2-pyridyl, 5-sulfonyl-methyl-2-pyridyl, 4-methoxy-2-pyridyl, 4-trifluoromethyl-2-pyridyl, 4-ethyl-2-pyridyl, 4-methyl-2-pyridyl, 6-chloro-2-pyridyl, 6-fluoro-2-pyridyl, 6-methyl-2-pyridyl, 6-ethyl-2-pyridyl, 6-trifluoromethyl-2-pyridyl, 6-methoxy-2-pyridyl, 6-sulfido-methyl-2-pyridyl, 6-sulfonylmethyl-2-pyridyl, 6-dimethylamino-2-pyridyl, phenyl, benzyl, 2-chloro-4-pyridyl, quinoxalin-2-yl, thiazol-2-yl, benzoxazol-2-yl, benzothiazol-2-yl, 3-fluorophenyl, 3-pyridyl, 3-bromo-2-pyridyl, 3-ethenyl-2-pyridyl and 5-ethenyl-2-pyridyl.

In particular embodiments of the compounds of formula (I), $R^3$ is hydrogen.

In particular embodiments of the compounds of formula (I), $R^6$ is absent. In other embodiments of the compounds of formula (I), $R^6$ is a halogen present at one ring carbon atom.

In one embodiment, the invention is directed to methods of treating a patient (preferably a human) for diseases in which the M1 receptor is involved, such as Alzheimer's Disease, cognitive impairment, schizophrenia, pain disorders and sleep disorders, by administering to the patient a therapeutically effective amount of a compound of general formula (I).

The invention is also directed to the use of a compound of formula (I) for treating diseases or disorders in which the M1 receptor is involved, such as Alzheimer's disease, cognitive impairment, schizophrenia, pain disorders and sleep disorders.

The invention is also directed to medicaments or pharmaceutical compositions for treating diseases or disorders in which the M1 receptor is involved, such as Alzheimer's disease, cognitive impairment, schizophrenia, pain disorders and sleep disorders, which comprise a compound of formula (I), or a pharmaceutically acceptable salt thereof, and a pharmaceutically acceptable carrier.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, comprising combining a compound of formula (I) with one or more pharmaceutically acceptable carriers.

Within the genus of compounds of formula (I), there is a sub-genus of compounds of formula (II):

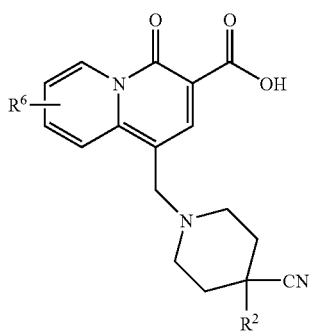

and pharmaceutically acceptable salts thereof, wherein $R^6$ is as described above, and $R^2$ is selected from the group consisting of
- (1) —$(CH_2)_n$-aryl, and
- (2) heteroaryl, wherein said aryl or heteroaryl moiety is optionally substituted with one or more
- (a) halogen,
- (b) hydroxy,
- (c) —O—$C_{1-6}$ alkyl
- (d) —$C_{1-6}$ alkyl,
- (e) —$C_{2-6}$ alkenyl; and n is 0, 1 or 2. Typically, $R^6$ is absent.

In another sub-genus within the genus of compounds of formula (I), there are compounds of formula (III):

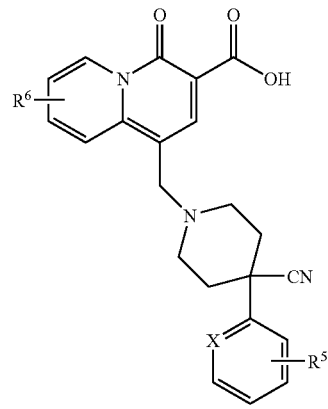

and pharmaceutically acceptable salts thereof, wherein $R^6$ is as described above, and X is selected from the group consisting of
- (1) CH, and
- (2) N, and $R^5$ is optionally present and is selected from the group consisting of
- (1) halogen,
- (2) hydroxy,
- (3) —O—$C_{1-6}$ alkyl,
- (4) —$C_{1-6}$ alkyl, and
- (5) —$C_{2-6}$ alkenyl. Typically, $R^6$ is absent.

Specific embodiments of formula (I) are described herein as Examples 1-50, such as
1-[(4-cyano-4-pyridin-2-ylpiperidin-1-yl)methyl]-4-oxo-4H-quinolizine-3-carboxylic acid (Example 1);
1-{[4-cyano-4-(4-methylpyridin-2-yl)piperidin-1-yl]methyl}-4-oxo-4H-quinolizine-3-carboxylic acid (Example 2);
1-{[4-cyano-4-(3-fluorophenyl)piperidin-1-yl]methyl}-4-oxo-4H-quinolizine-3-carboxylic acid (Example 46);
1-[(4-cyano-4-pyridin-3-ylpiperidin-1-yl)methyl]-4-oxo-4H-quinolizine-3-carboxylic acid (Example 47);
1-{[4-(3-bromopyridin-2-yl)-4-cyanopiperidin-1-yl]methyl}-4-oxo-4H-quinolizine-3-carboxylic acid (Example 48);
1-{[4-cyano-4-(3-vinylpyridin-2-yl)piperidin-1-yl]methyl}-4-oxo-4H-quinolizine-3-carboxylic acid (Example 49);
1-{[4-cyano-4-(5-vinylpyridin-2-yl)piperidine-1-yl]methyl}-4-oxo-4H-quinolizine-3-carboxylic acid (Example 50); and
Sodium 1-[(4-cyano-4-pyridin-2-ylpiperidin-1-yl)methyl]-9-methyl-4-oxo-4H-quinolizine-3-carboxylate (Example 51);
and pharmaceutically acceptable salts thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formulae (II) or (III), or a pharmaceutically acceptable salt thereof.

The invention is also directed to the use of a compound of formulae (II) or (III) for treating a disease or disorder in which the M1 receptor is involved, such as Alzheimer's Disease, cognitive impairment, schizophrenia, pain disorders and sleep disorders, by administering to the patient a compound of formulae (II) or (III), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formulae (II) or (III), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising combining a compound of formulae (II) or (III), or a pharmaceutically acceptable salt thereof, with a pharmaceutically acceptable carrier.

Where a variable occurs more than once in any of Formulas (I) to (III) or in a substituent thereof, the individual occurrences of that variable are independent of each other, unless otherwise specified.

As used herein, in particular in the definitions of $R^2$, $R^3$, $R^{4A}$, $R^{4B}$ and $R^6$, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, in particular in the definition of $R^2$, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, in particular in the definition of $R^2$, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkenyl groups include ethynyl and propynyl.

As used herein, in particular in the definitions of $R^2$, $R^3$, $R^{4A}$, $R^{4B}$ and $R^6$, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

As used herein, the term "halo" or "halogen" includes fluoro, chloro, bromo and iodo.

As used herein, in particular in the definition of $R^2$, the term "heteroaryl," by itself or as part of another substituent, means a cyclic or polycyclic group having ring carbon atoms and at least one ring heteroatom (O, N or S), wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

Preferred $R^2$ heteroaryl groups have from 5 to 12 ring atoms. In one such embodiment, the heteroaryl groups have 5 or 6 ring atoms.

For example, one subgroup of $R^2$ heteroaryl groups have 5 or 6 ring atoms and a single heteroatom, which is nitrogen. Exemplary heteroaryl groups in this embodiment are pyridyl and pyrrolyl.

Another subgroup of $R^2$ heteroaryl groups have 5 or 6 ring atoms and two heteroatoms, which are selected from sulfur and nitrogen. Exemplary heteroaryl groups in this embodiment are pyrazolyl, imidazolyl, thienyl and isothiazolyl.

Another subgroup of $R^2$ heteroaryl groups have 7 or 8 ring atoms and two heteroatoms, which are selected from oxygen, sulfur and nitrogen. Exemplary heteroaryl groups in this embodiment are benzoxazolyl, benzothiazolyl and quinoxalinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formulae (I) to (III).

Formulae (I) to (III) are shown above without a definite stereochemistry at certain positions. The present invention includes all stereoisomers of formulae (I) to (III) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

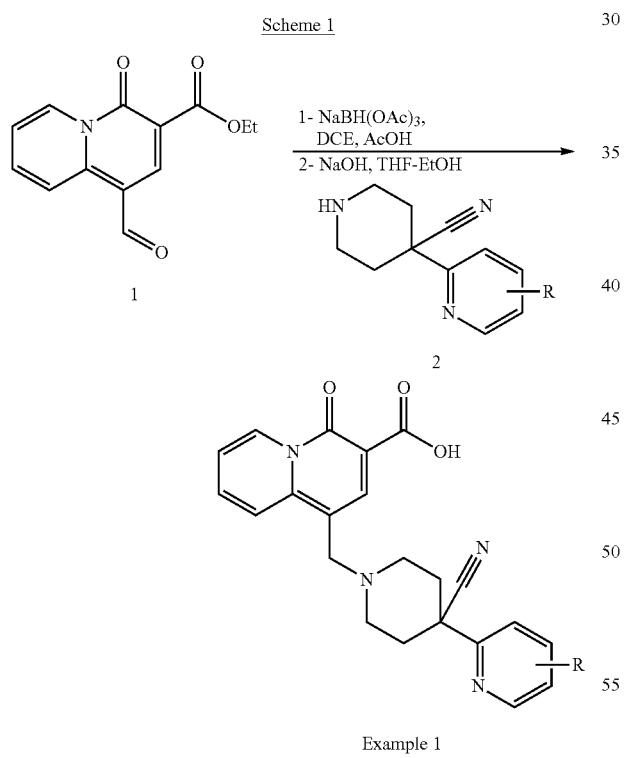

Example 1

Compound 1 is described in the literature (*J. Am. Chem. Soc.*; 126; 50; 2004; 16353-16360) and can undergo reductive amination with an amine such as 2 using a reducing agent like sodium cyanoborohydride in an appropriate solvent (such as DCE or THF). Hydrolysis of the ester group can be carried out using a base like sodium hydroxide in solvents such as THF, ethanol, or DMSO (and optionally an acid, such as citric acid) to afford Example 1.

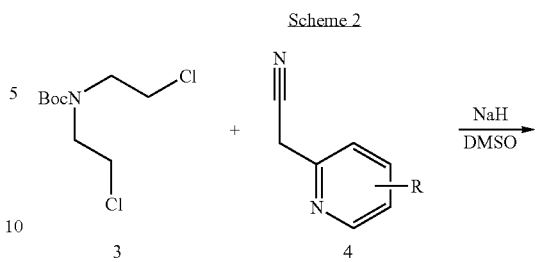

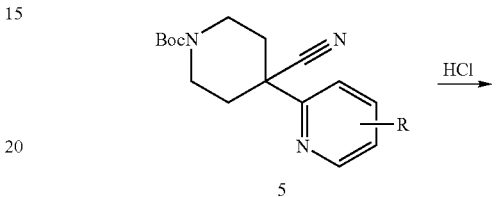

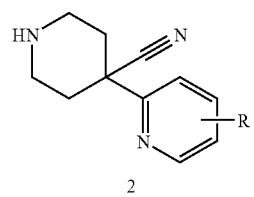

Amines such as 2 may be prepared as shown in Scheme 2. Bis-alkylation of the appropriate cyanomethyl derivative 4 with a suitably protected bis-(choroethyl)amine may be carried out using a base like sodium hydride in DMSO to afford product 5. Removal of the Boc protecting can be done out using an acid such as HCl in a solvent like ethyl acetate to afford compound 2.

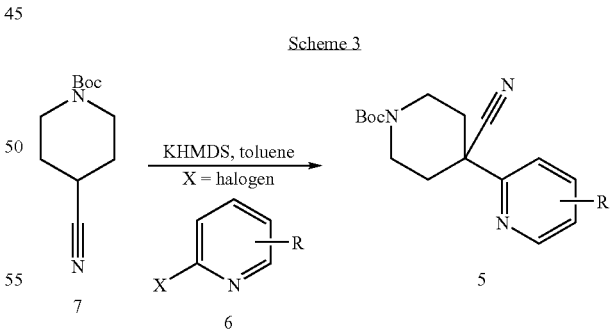

Alternatively, as shown in Scheme 3, compounds such as 2 may be prepared via nucleophilic displacement of a halopyridine (for example, 2-fluoropyridine and 2-chloropyridine) such as 6 with anion of 7 in a solvent like toluene or THF. The anion of compound 7 may be generated using a base like potassium hexamethyldisilazane, lithium bis(trimethylsilyl) amide (LHMDS) or lithium diisopropylamide.

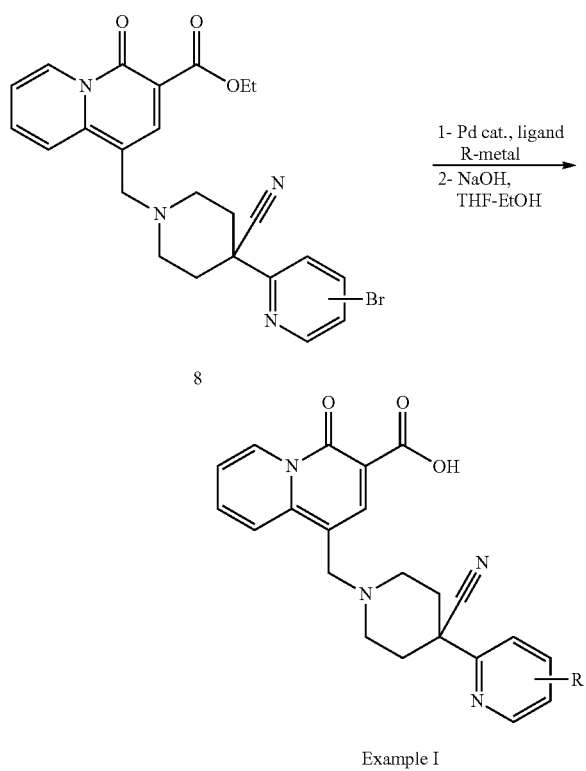

Scheme 4

Example I

An additional approach to compounds of example 1 is shown in Scheme 4. The appropriate halo (chloro, bromo, or iodo) substituted pyridine 8 may be prepared as described in Schemes 1-3 and can undergo cross coupling using a transition metal such as palladium in the presence of a phosphine ligand in a solvent like DMSO with the appropriate organometallic reagent. For example, the organometallic reagent may be aromatic or alkyl, and the metal can be tin, boron, zinc, or magnesium. Ester hydrolysis as previously shown in Scheme 1 affords the final example.

The present invention also provides a method for the synthesis of compounds useful as intermediates in the preparation of compounds of the invention.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1991. The protecting groups may be removed at a convenient sequent stage using methods known from the art.

Specific embodiments of the compounds of the invention, and methods of making them, are described in the Examples herein.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther*, 1993, 58:319-379; *Eur J Pharmacol*, 1996, 295:93-102, and *Mol Pharmacol*, 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

The present invention is directed to the use of the compounds of formulas (I) to (III) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases mediated by the muscarinic M1 receptor, such as schizophrenia SCHIZOsleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another specific embodiment, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexyl, bromocriptine, biperiden, chiorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night tenor; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists, such as ABT089, SSR180711 and MEM63908; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; $GABA_A$ inverse agonists; GSK3β inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists and dopamine receptor agonists such as alentemol, bromocriptine, fenoldopam, lisuride, naxagolide, pergolide and pramipexole.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the schemes and examples herein. Starting materials are made according to procedures known in the art or as illustrated herein. The following examples are provided so that the invention might be more fully understood.

The following examples are provided to illustrate the invention and are not to be construed as limiting the scope of the invention in any manner.

EXAMPLE 1

1-[(4-cyano-4-pyridin-2-ylpiperidin-1-yl)methyl]-4-oxo-4H-quinolizine-3-carboxylic acid

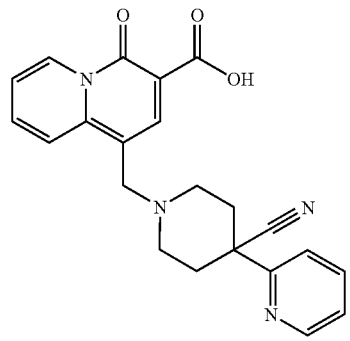

A mixture of tert-butyl 4-cyanopiperidine-1-carboxylate (220 mg, 1.05 mmol) and 2-fluoropyridine (0.094 mL, 1.10 mmol) was dissolved in 5.2 mL of THF. The reaction was purged with a stream of nitrogen and cooled to −78° C. To this reaction was added 1M sodium bis(trimethylsilyl)amide in THF (1.47 mL, 1.47 mmol), which was stirred for 1 hour. The reaction was warmed to ambient temperature, stirred for 1 hour, and quenched with a saturated ammonium chloride solution. The mixture was extracted with dichloromethane (3×10 mL). The combined organic extracts were dried over sodium sulfate, filtered, concentrated, and subjected to silica gel chromatography eluting with 0-20% EtOAc in hexanes. Collection of product containing fractions and removal of solvent yielded tert-butyl 4-cyano-4-pyridin-2-ylpiperidine-1-carboxylate.

The above carboxylate (3.11 g, 10.8 mmol) was dissolved in 54 mL of dry EtOAc and cooled to 0° C. Anhydrous HCl gas was then bubbled through the solution for 5 minutes. The reaction was warmed to ambient temperature and stirred for 2 hours. The reaction mixture was taken up in dichloromethane (100 mL) and slowly neutralized with a saturated sodium bicarbonate solution. The mixture was partitioned between water and dichloromethane. The aqueous layer was extracted with dichloromethane (6×50 mL). The combined organic extracts were dried over sodium sulfate, filtered, and concentrated to yield 4-pyridin-2-ylpiperidine-4-carbonitrile.

In a 10-20 mL Emrys™ process vial, a mixture of the ethyl 1-formyl-4-oxo-4H-quinolizine-3-carboxylate (684 mg, 2.79 mmol), 4-pyridin-2-ylpiperidine-4-carbonitrile (627 mg, 3.35 mmol), glacial acetic acid (0.96 mL, 16.7 mmol) and 4.1 mL of dichloroethane was stirred vigorously. To the stirring mixture was added resin-bound MP-cyanoborohydride (2.74 g, 5.58 mmol). The mixture was heated via Emrys Optimizer™ microwave to 120° C. for 30 minutes. Filtration and solvent removal provided material, which was subjected to silica gel chromatography eluting with 55-75% EtOAc in hexanes. Collection of product containing fractions and removal of solvent afforded the ethyl 4-[(4-cyano-4-pyridin-2-ylpiperidin-1-yl)methyl]-1-oxo-1,8a-dihydronaphthalene-2-carboxylate.

The above carboxylate (705 mg, 1.69 mmol) was dissolved in a 2:1 THF:EtOH solution (8.4 mL), treated with 1N NaOH (1.78 mL, 1.78 mmol), and warmed to 60° C. for 16 hours. The reaction was reduced in volume under vacuum, providing material, which was subjected to preparative reverse phase HPLC. Collection of product containing fractions and removal of solvent yielded the title compound, which was converted to the sodium salt via treatment with 1N NaOH (2.74 mL, 2.74 mmol). After 1 hour, the reaction was concentrated to dryness and washed with a minimum amount of cold water (5 mL) via Buchner funnel. The residue was dissolved using methanol and the solution was concentrated in vacuo to afford the title compound that gave a proton NMR spectrum consistent with theory and a high resolution mass spectrum (ES+) m/z of 389.1626 calculated for M+H$^+$[C$_{22}$H$_{20}$N$_4$O$_3$: 389.1608]: $^1$H NMR (500 MHz, CD$_3$OD) δ 9.37 (d, J=7.2 Hz, 1H), 8.55 (d, J=3.9 Hz, 1H), 8.30 (s, 1H), 8.18 (d, J=8.9 Hz, 1H), 7.85 (t, J=7.8 Hz, 1H), 7.69 (t, J=6.3 Hz, 1H), 7.62 (d, J=8.0 Hz, 1H), 7.32-7.36 (m, 1H), 7.29 (t, J=7.0 Hz, 1H), 3.82 (s, 2H), 3.09 (d, J=12.2 Hz, 2H), 2.55 (t, J=12.1 Hz, 2H), 2.23 (t, J=12.7 Hz, 2H), 2.13 (d, J=11.7 Hz, 2H).

EXAMPLE 2

1-{[4-cyano-4-(4-methylpyridin-2-yl)piperidin-1-yl]methyl}-4-oxo-4H-quinolizine-3-carboxylic acid

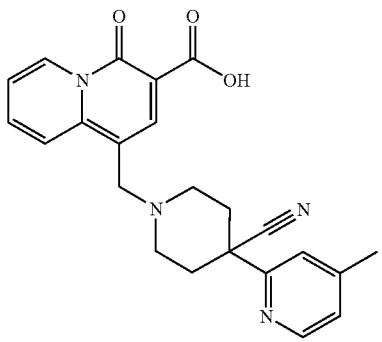

A mixture of tert-butyl 4-cyanopiperidine-1-carboxylate (15.2 g, 72.3 mmol) and 2-fluoro-4-methylpyridine (9.64 g, 87.0 mmol) was dissolved in 361 mL of THF. The reaction was purged with a stream of nitrogen and cooled to −78° C. To this reaction was added 1.0 M sodium bis(trimethylsilyl)amide in THF (101 mL, 101 mmol), which was stirred for 1 hour. The reaction was warmed to ambient temperature, stirred for 36 hours, and quenched with a saturated ammonium chloride solution. The mixture was extracted with dichloromethane (3×200 mL). The combined organic extracts were dried over sodium sulfate, filtered, concentrated, and subjected to silica gel chromatography eluting with 0-25% EtOAc in hexanes to yield tert-butyl 4-cyano-4-(4-methylpyridin-2-yl)piperidine-1-carboxylate.

The above carboxylate (12.8 g, 42.5 mmol) was dissolved in a 1:1 EtOAc:DCM (424 mL) and was cooled to 0° C. Anhydrous HCl gas was then bubbled through the solution for 5 minutes. The reaction was warmed to ambient temperature and stirred for 1 hour. The reaction mixture was concentrated of volatiles and slowly neutralized with a saturated sodium bicarbonate solution. The resulting slurry was washed with 10% MeOH in DCM and filtered through a Buchner funnel in vacuo. The filtrate was concentrated to give 4-(4-methylpyridin-2-yl)piperidine-4-carbonitrile.

A mixture of the ethyl 1-formyl-4-oxo-4H-quinolizine-3-carboxylate (2.60 g, 10.6 mmol), 4-(4-methylpyridin-2-yl)piperidine-4-carbonitrile (1.78 g, 8.83 mmol), and 36.8 mL of anhydrous THF was cooled to 10° C. and stirred vigorously. To the stirring mixture was added sodium triacetoxyborohydride (2.62 g, 12.4 mmol), portionwise over a period of 1 hour. The mixture was heated to 50° C. for 18 hours. The reaction was quenched with a 10% sodium bicarbonate solution and extracted with EtOAc (3×50 mL). The organic layers were combined, acidified with 1 N HCl, and extracted with DCM (8×150 mL). In a 500 mL Erlenmeyer flask, the aqueous layer was neutralized slowly with solid sodium carbonate under continuous stirring until pH ~7-8 and then extracted with DCM (3×200 mL). The organic extracts were combined, dried over sodium sulfate, filtered, and concentrated to afford the ethyl 1-{[4-cyano-4-(4-methylpyridin-2-yl)piperidin-1-yl]methyl}-4-oxo-4H-quinolizine-3-carboxylate that gave a proton NMR spectrum consistent with theory and a mass spectrum (ES+) m/z of 431.0 calculated for M+H$^+$: $^1$H NMR (400 MHz, CDCl$_3$) δ 9.51 (d, J=7.1 Hz, 1H), 8.43 (d, J=4.95 Hz, 1H), 8.32 (s, 1H), 8.14 (d, J=8.9 Hz, 1H), 7.70 (t, J=7.8 Hz, 1H), 7.43 (s, 1H), 7.26 (m, 1H), 7.06 (d, J=4.9 Hz, 1H), 4.44 (q, J=7.1 Hz, 2H), 3.75 (s, 2H), 3.01 (d, J=12.0 Hz, 2H), 2.56 (t, J=11.3 Hz, 2H), 2.39 (s, 3H), 2.29 (t, J=12.9 Hz, 2H), 2.05 (d, J=12.4 Hz, 2H), 1.44 (t, J=7.1 Hz, 3H).

The above carboxylate (1.55 g, 3.60 mmol) was dissolved in a 2:1 THF:EtOH solution (36 mL), treated with 1 N NaOH (3.78 mL, 3.78 mmol), and warmed to 50° C. for 20 hours. The reaction temperature was increased to 60° C. for 2 hours. The reaction was treated with additional 1 N NaOH (0.18 mL, 0.18 mmol) and warmed to 70° C. for 4 hours. The reaction was reduced in volume under vacuum, diluted with deionized water (50 mL), and extracted with EtOAc (2×100 mL). The aqueous layer was concentrated to dryness to afford the title compound that gave a proton NMR spectrum consistent with theory and a high resolution mass spectrum (ES+) m/z of 403.1772 calculated for M+H$^+$[C$_{23}$H$_{22}$N$_4$O$_3$: 403.1765]: $^1$H NMR (500 MHz, CD$_3$OD) δ 9.36 (d, J=7.3 Hz, 1H), 8.38 (d, J=5.0 Hz, 1H), 8.29 (s, 1H), 8.18 (d, J=9.0 Hz, 1H), 7.68 (t, J=7.5 Hz, 1H), 7.45 (s, 1H), 7.29 (t, J=6.7 Hz, 1H), 7.18 (d, J=5.0 Hz, 1H), 3.81 (s, 2H), 3.09 (d, J=12.1 Hz, 2H), 2.51 (t, J=10.9 Hz, 2H), 2.40 (s, 3H), 2.21 (t, J=12.7 Hz, 2H), 2.11 (d, J=12.1 Hz, 2H).

The following compounds were prepared according to the general procedure provided in Example 1. The starting materials are either commercially available, known in the literature or may be prepared from commercially available reagents using conventional reactions well known in the art.

| Ex. | R$^2$ | R$^1$ | M + H |
|---|---|---|---|
| 3 | Ph | CN | 388.1673 |
| 4 | 4-fluorophenyl | CN | 406.1 |
| 5 | 2-fluorophenyl | CN | 406.15 |
| 6 | 2,4-difluorophenyl | CN | 424.12 |
| 7 | 4-cyanophenyl | CN | 413.0 |

25
-continued

[Structure: quinolizinone carboxylic acid with CH2-piperidine(R1,R2) substituent]

| Ex. | R² | R¹ | M + H |
|---|---|---|---|
| 8 | 3-methylphenyl | CN | 402.0 |
| 9 | 2-methylphenyl | CN | 402.18 |
| 10 | 2-methoxyphenyl | CN | 418.1792 |
| 11 | 3-fluoro-2-pyridyl | CN | 407.0 |
| 12 | 3-bromo-2-pyridyl | CN | 468.8 |
| 13 | 4-methyl-2-pyridyl | CN | 403.1777 |
| 14 | 5-bromo-2-pyridyl | CN | 496.9 |
| 15 | 5-methyl-2-pyridyl | CN | 403.0 |
| 16 | 5-fluoro-2-pyridyl | CN | 407.0 |

26
-continued

[Structure: quinolizinone carboxylic acid with CH2-piperidine(R1,R2) substituent]

| Ex. | R² | R¹ | M + H |
|---|---|---|---|
| 17 | 5-chloro-2-pyridyl | CN | 422.9 |
| 18 | 5-cyano-2-pyridyl | CN | 414.0 |
| 19 | 5-trifluoromethyl-2-pyridyl | CN | 456.9 |
| 20 | 5-ethyl-2-pyridyl | CN | 417.0 |
| 21 | 5-ethynyl-2-pyridyl | CN | 413.0 |
| 22 | 5-methoxy-2-pyridyl | CN | 419.0 |
| 23 | 5-methylthio-2-pyridyl | CN | 435.0 |
| 24 | 5-methylsulfonyl-2-pyridyl | CN | 467.0 |
| 25 | 4-methoxy-2-pyridyl | CN | 419.1740 |
| 26 | 4-trifluoromethyl-2-pyridyl | CN | 457.1496 |

-continued

| Ex. | R² | R¹ | M + H |
|---|---|---|---|
| 27 | 4-Et-pyridin-2-yl | CN | 417.1941 |
| 28 | 6-Cl-pyridin-2-yl | CN | 422.9 |
| 29 | 6-F-pyridin-2-yl | CN | 407.0 |
| 30 | 6-Me-pyridin-2-yl | CN | 403.0 |
| 31 | 6-Et-pyridin-2-yl | CN | 435.0 |
| 32 | 6-CF₃-pyridin-2-yl | CN | 456.9 |
| 33 | 6-OMe-pyridin-2-yl | CN | 419.0 |
| 34 | 6-SMe-pyridin-2-yl | CN | 435.0 |

-continued

| Ex. | R² | R¹ | M + H |
|---|---|---|---|
| 35 | 4-SO₂Me-pyridin-2-yl | CN | 466.9 |
| 36 | 6-N(Me)₂-pyridin-2-yl | CN | 432.0 |
| 37 | Ph | COCH₃ | 405.0 |
| 38 | Ph | Ph | 439.2040 |
| 39 | Bn | CO₂CH₂CH₃ | 449.0 |
| 40 | Ph | OH | 379.1654 |
| 41 | 2-Cl-pyridin-4-yl (4-methyl) | CN | 423.1236 |
| 42 | quinoxalin-2-yl | CN | 439.9 |
| 43 | 5-methyl-thiazol-2-yl | CN | 408.9 |
| 44 | benzoxazol-2-yl | CN | 429.0 |
| 45 | benzothiazol-2-yl | CN | 445.0 |

EXAMPLE 46

1-{[4-cyano-4-(3-fluorophenyl)piperidin-1-yl]methyl}-4-oxo-4H-quinolizine-3-carboxylic acid

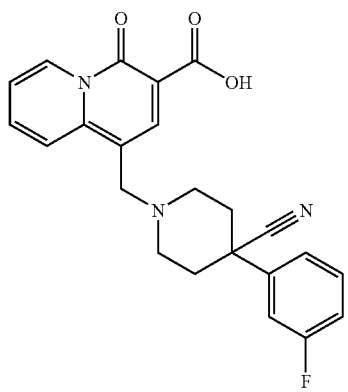

2-Chloro-N-(2-chloroethyl)ethanaminium chloride (12.5 g, 70.2 mmol) was stirred in 351 mL of THF. To this mixture was added triethylamine (10.3 mL, 73.7 mmol) and then di-tert-butyl dicarbonate (16.1 g, 73.7 mmol), which was stirred for 19 hours. The reaction was diluted with dichloromethane (250 mL), washed with water (3×250 mL), and partitioned between water and dichlormethane. The organic layer was dried over sodium sulfate, filtered, and concentrated to afford tert-butyl bis(2-chloroethyl)carbamate.

A mixture of 3-fluorophenylacetonitrile (200 mg, 1.48 mmol) and tert-butyl bis(2-chloroethyl)carbamate (358 mg, 1.48 mmol) was dissolved in 14.8 mL of anhydrous DMSO. The reaction was purged with a stream of nitrogen and cooled to 18° C. To this reaction was added sodium hydride (358 mg, 1.48 mmol), which was then warmed to ambient temperature and stirred for 2 hours. The reaction was warmed to 50° C. and stirred for 17 hours. The mixture was diluted with dichloromethane (40 mL), washed with water (3×40 mL), and partitioned between water and dichloromethane. The organic layer was dried over sodium sulfate, filtered, concentrated, and subjected to silica gel chromatography eluting with 0-20% EtOAc in hexanes. Collection of product containing fractions and removal of solvent yielded tert-butyl 4-cyano-4-(3-fluorophenyl)piperidine-1-carboxylate.

The title compound was prepared in a manner analogous to that described in Example 1 that gave a proton NMR spectrum consistent with theory and a high resolution mass spectrum (ES+) m/z of 406.1575 calculated for M+H+ [$C_{23}H_{20}F_1N_3O_3$: 406.1562]: $^1$H NMR (500 MHz, CD$_3$OD) δ 9.56 (d, J=7.1 Hz, 1H), 8.70 (s, 1H), 8.47 (d, J=9.0 Hz, 1H), 8.18 (t, J=7.9 Hz, 1H), 7.72 (t, J=6.8 Hz, 1H), 7.46-7.51 (m, 1H), 7.37 (d, J=8.6 Hz, 1H), 7.30 (d, J=10.0 Hz, 1H), 7.16 (t, J=8.4 Hz, 1H), 4.67 (bs, 2H), 3.65 (m, 2H), 3.37 (m, 2H), 2.46 (d, J=14.2 Hz, 2H), 2.29 (m, 2H).

EXAMPLE 47

1-[(4-cyano-4-pyridin-3-ylpiperidin-1-yl)methyl]-4-oxo-4H-quinolizine-3-carboxylic acid

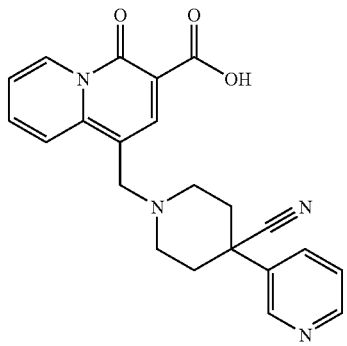

The title compound was prepared as the trifluoroacetate salt in a manner analogous to that described in Example 20 that gave a proton NMR spectrum consistent with theory and a high resolution mass spectrum (ES+) m/z of 389.1614 calculated for M+H+ [$C_{22}H_{20}N_4O_3$: 389.1608]: $^1$H NMR (500 MHz, CD$_3$OD) δ 9.57 (d, J=7.1 Hz, 1H), 8.82 (s, 1H), 8.74 (s, 1H), 8.66 (s, 1H), 8.47 (d, J=8.55 Hz, 1H), 8.18 (t, J=7.8 Hz, 1H), 8.12 (d, J=7.8 Hz, 1H), 7.72 (t, J=7.0 Hz, 1H), 7.63 (m, 1H), 4.78 (s, 2H), 3.76 (m, 2H), 3.48 (m, 2H), 2.56 (d, J=13.4 Hz, 2H), 2.42 (m, 2H).

EXAMPLE 48

1-{[4-(3-bromopyridin-2-yl)-4-cyanopiperidin-1-yl]methyl}-4-oxo-4H-quinolizine-3-carboxylic acid

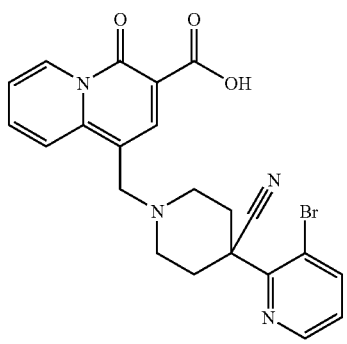

3-Bromo-2-methylpyridine (10.0 g, 58.1 mmol), diphenylperoxyanhydride (2.82 g, 11.6 mmol), 1-bromopyrrolidine-2,5-dione (10.9 g, 61.0 mmol) were refluxed in 233 mL of carbon tetrachloride for 144 hours. The reaction mixture was cooled to ambient temperature and washed with water (3×200 mL). The organic layer was dried over Na$_2$SO$_4$, filtered, concentrated, and purified by silica gel chromatography eluting with 0-30% EtOAc in hexanes to provide 3-bromo-2-(bromomethyl)pyridine.

The above pyridine (5.13 g, 20.4 mmol) was stirred in 50.1 mL of a 5.6:1 solution of ethanol:deionized water. To this mixture was added sodium cyanide (1.20 g, 24.5 mmol), which was stirred for 2 hours and 30 minutes. The reaction mixture was diluted with dichloromethane (100 mL), washed with water (3×100 mL), and partitioned between water and dichloromethane. The organic layer was dried over sodium sulfate, filtered, concentrated, and subjected to silica gel chromatography eluting with 5-30% EtOAc in hexanes to yield (3-bromopyridin-2-yl)acetonitrile.

The (3-bromopyridin-2-yl)acetonitrile (2.00 g, 10.2 mmol) and tert-butyl bis(2-chloroethyl)carbamate (2.46 g, 10.2 mmol) were dissolved in 102 mL of DMSO. The reaction was purged with a stream of nitrogen and cooled to 18° C. To this reaction was added sodium hydride (0.564 g, 22.3 mmol), which was then warmed to 50° C. and stirred for 18 hours. The mixture was diluted with dichloromethane (150 mL), washed with water (3×150 mL), and partitioned between water and dichloromethane. The organic layer was dried over sodium sulfate, filtered, concentrated, and subjected to silica gel chromatography eluting with 5-30% EtOAc in hexanes to yield tert-butyl 4-(3-bromopyridin-2-yl)-4-cyanopiperidine-1-carboxylate.

The above carboxylate (290 mg, 0.79 mmol) was dissolved in 7.9 mL of a 1:1 solution of dry EtOAc:dichloromethane and cooled to 0° C. Anhydrous HCl gas was then bubbled through the solution for 5 minutes. The reaction was warmed to ambient temperature and stirred for 2 hours. The reaction mixture was taken up in dichloromethane (10 mL) and slowly neutralized with a saturated sodium bicarbonate solution. The mixture was partitioned between water and dichloromethane. The aqueous layer was extracted with dichloromethane (6×10 mL). The combined organic extracts were dried over sodium sulfate, filtered, and concentrated to yield 4-(3-bromopyridin-2-yl)piperidine-4-carbonitrile.

In a 2-5 mL Emrys™ process vial, a mixture of the ethyl 1-formyl-4-oxo-4H-quinolizine-3-carboxylate (150 mg, 0.61 mmol), 4-pyridin-2-ylpiperidine-4-carbonitrile (179 mg, 0.67 mmol), glacial acetic acid (0.21 mL, 3.67 mmol) and 3.1 mL of dichloroethane was stirred vigorously. To the stirring mixture was added resin-bound MP-cyanoborohydride (600 mg, 1.22 mmol). The mixture was heated via Emrys Optimizer™ microwave to 120° C. for 20 minutes. Filtration and solvent removal provided crude material, which was purified by preparative reverse phase HPLC to afford ethyl 1-{[4-(3-bromopyridin-2-yl)-4-cyanopiperidin-1-yl]methyl}-4-oxo-4H-quinolizine-3-carboxylate.

The ethyl 1-{[4-(3-bromopyridin-2-yl)-4-cyanopiperidin-1-yl]methyl}-4-oxo-4H-quinolizine-3-carboxylate (30 mg, 0.061 mmol) was dissolved in DMSO (1.0 mL), treated with lithium hydroxide (0.15 mL, 0.80 mmol), and warmed to ambient temperature for 96 hours. The reaction mixture was purified by preparative reverse phase HPLC to yield the title compound as the trifluoroacetate salt that gave a proton NMR spectrum consistent with theory and a low resolution mass spectrum (ES+) m/z of 468.8 calculated for M+H$^+$ [$C_{22}H_{19}BrN_4O_3$]: $^1$H NMR (400 MHz, CD$_3$OD) δ 9.57 (d, J=6.8 Hz, 1H), 8.75 (s, 1H), 8.59 (m, 1H), 8.46 (d, J=8.9 Hz, 1H), 8.16-8.22 (m, 2H), 7.73 (t, J=7.1 Hz, 1H), 7.37 (dd, J=4.6 Hz, 1H), 3.77 (bs, 2H), 3.59 (t, J=12.0 Hz, 2H), 2.84 (m, 2H), 2.65 (m, 2H).

EXAMPLE 49

1-{[4-cyano-4-(3-vinylpyridin-2-yl)piperidin-1-yl]methyl}-4-oxo-4H-quinolizine-3-carboxylic acid

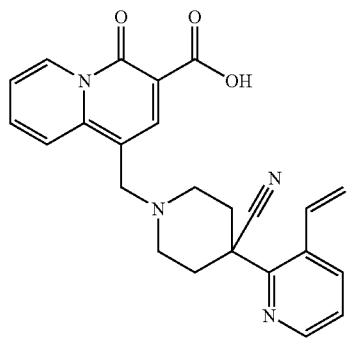

In a 2-5 mL Emrys™ process vial, the ethyl 1-{[4-(3-bromopyridin-2-yl)-4-cyanopiperidin-1-yl]methyl}-4-oxo-4H-quinolizine-3-carboxylate (50 mg, 0.10 mmol) was dissolved in 0.40 mL of anhydrous THF and treated with potassium vinyltrifluoroborate (40.6 mg, 0.30 mmol) and 1M cesium carbonate solution (0.20 mL, 0.20 mmol). The reaction was purged with a stream of nitrogen, charged with bis(tri-tert-butylphosphine)palladium(0) (5.2 mg, 0.010 mmol), and heated via Emrys Optimizer™ microwave to 160° C. for 10 minutes. Filtration and solvent removal provided material, which was subjected to preparative reverse phase HPLC. Collection of product containing fractions and removal of solvent afforded the ethyl 1-{[4-cyano-4-(3-vinylpyridin-2-yl)piperidin-1-yl]methyl}-4-oxo-4H-quinolizine-3-carboxylate.

The title compound was prepared as the trifluoroacetate salt in a manner analogous to that described in Example 1 that gave a low resolution mass spectrum (ES+) m/z of 415.0 calculated for M+H$^+$[$C_{24}H_{22}N_4O_3$]: $^1$H NMR (400 MHz, CD$_3$OD) δ 9.57 (d, J=7.1 Hz, 1H), 8.74 (s, 1H), 8.50 (s, 1H), 8.45 (d, J=9.1 Hz, 1H), 8.19 (t, J=8.0 Hz, 1H), 7.99 (d, J=7.6 Hz, 1H), 7.72 (t, J=7.1 Hz, 1H), 7.42-7.48 (m, 2H), 5.82 (d, J=17.0 Hz, 1H), 5.61 (d, J=0.9 Hz, 1H), 3.75 (bs, 2H), 3.59 (t, J=13.5 Hz, 2H), 2.55-2.65 (m, 4H).

EXAMPLE 50

1-{[4-cyano-4-(5-vinylpyridin-2-yl)piperidine-1-yl]methyl}-4-oxo-4H-quinolizine-3-carboxylic acid

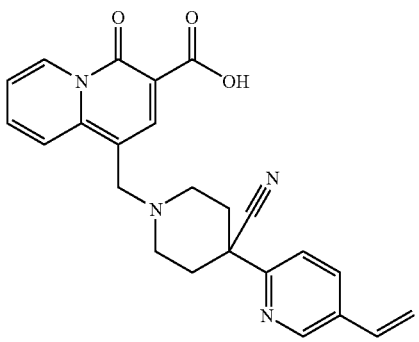

The title compound was prepared in a manner analogous to that described in Examples 1 and 22 that gave a low resolution mass spectrum (ES+) m/z of 415.0 calculated for M+H$^+$ [$C_{24}H_{22}N_4O_3$].

EXAMPLE 51

Sodium 1-[(4-cyano-4-pyridin-2-ylpiperidin-1-yl)methyl]-9-methyl-4-oxo-4H-quinolizine-3-carboxylate

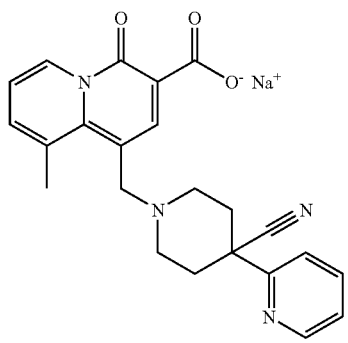

To a solution of LDA (1.8 M in THF/heptane/ethylbenzene, 64.8 mL, 117 mmol) in THF (200 mL) at −78° C. was added 2,3-lutidine (10.6 mL, 93.3 mmol) in THF (62 mL) dropwise over 10 min. After stirring the mixture an additional 40 min at −78° C., diethyl ethoxymethylenemalonate (21.7 mL, 107 mmol) in THF (30 mL) was added slowly over 15 min. The mixture was warmed slowly to rt over 2.5 h. The resulting solution was quenched with saturated aqueous $NH_4Cl$ and extracted with $CH_2Cl_2$ (3×). The combined extracts were dried ($Na_2SO_4$) and concentrated. The intermediate was dissolved in o-xylene (93 mL) and heated to reflux for 16 h. After cooling to rt, the mixture was concentrated. Purification by silica gel chromatography eluting with 0-5% $MeOH:CH_2Cl_2$ afforded ethyl 9-methyl-4-oxo-4H-quinolizine-3-carboxylate as a yellow solid.

To a solution of the above quinolizidinone (15.3 g, 66.2 mmol) in DMF (100 mL) at 0° C. was added $POCl_3$ (15.4 mL, 165 mmol) dropwise over 20 min via an addition funnel. The mixture was warmed to rt and stirred for 20 h. The resulting solution was poured into a 1 L Erlenmeyer flask containing iced water (300 mL). The resulting slurry was cooled in an ice bath and a yellow-brown precipitate formed. The solid was filtered and washed with water and ether. The solid was collected and dried in vacuo to afford ethyl 1-formyl-9-methyl-4-oxo-4H-quinolizine-3-carboxylate. as a yellow solid.

The above aldehyde was processed to sodium 1-[(4-cyano-4-pyridin-2-ylpiperidin-1-yl)methyl]-9-methyl-4-oxo-4H-quinolizine-3-carboxylate following the same procedure as described above in Example 1.
Sodium 1-[(4-cyano-4-pyridin-2-ylpiperidin-1-yl)methyl]-9-methyl-4-oxo-4H-quinolizine-3-carboxylate. $^1H$ NMR (400 MHz, $CD_3OD$) δ 9.37 (d, J=7.2 Hz, 1H), 8.50 (br d, J=4.9 Hz, 1H), 8.23 (s, 1H), 7.80 (dt, J=1.9, 7.6 Hz, 1H), 7.57 (d, J=8.1 Hz, 1H), 7.46 (d, J=7.2 Hz, 1H), 7.29 (ddd, J=1.1, 4.9, 7.6 Hz, 1H), 7.09 (t, J=7.2 Hz, 1H), 3.85 (s, 2H), 2.99 (m, 2H), 2.97 (s, 3H), 2.47 (t, J=11.8 Hz, 2H), 2.15 (t, J=13.1 Hz, 2H), 2.09 (t, J=13.1 Hz, 2H); ESI-HRMS ($MH^+$) calcd for $C_{23}H_{23}N_4O_3$ 403.1765. Found 403.1771.

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a $FLIPR^{384}$ Fluorometric Imaging Plate Reader System. The assay studies the effect of one or several concentrations of test compounds on basal or acetylcholine-stimulated $Ca^{2+}$ levels using FLIPR.

Compounds are prepared and subjected to a preincubation period of 4 min. Thereafter, a single $EC_{20}$ concentration of acetylcholine is added to each well (3 nM final). The intracellular $Ca^{2+}$ level of each sample is measured and compared to an acetylcholine control to determine any modulatory activity.

Cells: CHOnfat/hM1, hM2, hM3 or hM4 cells are plated 24 hr before the assay at a density of 18,000 cells/well (100 μL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 ug/ml hygromycin is added.

Equipment: 384 well plate, 120 μL addition plate; 96-well Whatman 2 ml Uniplate Incubator, 37° C., 5% $CO_2$; Skatron EMBLA-384 Plate Washer; Multimek Pipetting System; Genesis Freedom 200 System; Mosquito System; Temo Nanoliter Pipetting System; and $FLIPR^{384}$ Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 uM in buffer for a final concentration of 1 μM in Assay. 20% Pluronic Acid Solution stock, with concentration of 0.04% in Buffer, 0.02% in Assay.

65 μL of 2 mM Fluo-4AM are mixed with 130 μL of 20% Pluronic Acid. The resulting solution and 650 μL FBS is added to the assay buffer for a total volume of 65 mL. Positive Controls: 4-Br-A23187: 10 mM in DMSO; final concentration 10 μM. Acetylcholine: 10 mM in water, working stock at both 20 uM and 30 uM in assay buffer, final concentration of 10 μM. This is used to check the maximum stimulation of the CHOK1/hM1 cells. 20 uM (2×) acetylcholine is added in the preincubation part of the assay, and the 30 uM (3×) stock is added in the second part. ($EC_{20}$)Acetylcholine: 10 mM in water, working stock of 9 nM (3×), and final concentration in assay is 3 nM. This is used after the preincubation with test compounds. Addition of the $EC_{20}$) Acetylcholine to each well with a test compound will ascertain any modulator activity. 24 wells contain 3 nM Acetylcholine alone as a control.

Determining Activity of Putative Compounds:
Screening Plate Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanoliter Pipetting System by transferring 1 ul of serial diluted compounds to each well, and 1 mM acetylcholine (100× stock concentration) were added as a control. Using Temo, 49 μl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 uM acetylcholine control (3×) is added into control wells, and the 3× agonist plate is transferred into a 384 well plate.

Cells are washed three times with 100 μL of buffer, leaving 30 μL of buffer in each well. Using Multimek, 30 μL of Dye Loading Buffer is added into each well and incubated at 3° C., 5% $CO_2$ for up to one hr.

After 60 min, the cells are washed three times with 100 μL of buffer, leaving 30 μL of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

4 min of preincubation with the test compounds is provided to determine any agonist activity on the M1 receptor by comparison to the 1 mM acetylcholine control. After preincubation, the $EC_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 10 μM (10,000 nM) or less. The inflection point is calculated from the FLIPR values, and is a measure of activity. Such a result is indicative of the intrinsic activity of the compounds in use as M1 allosteric modulators.

IP values from the aforementioned assay for representative exemplary compounds of the invention (as described herein) are provided below in Table 1 below:

| Example | IP Value (nM) |
|---|---|
| 1 | 140 |
| 3 | 152 |
| 8 | 87 |
| 10 | 164 |
| 28 | 133 |
| 42 | 1241 |
| 45 | 91 |
| 46 | 562 |
| 47 | 363 |
| 48 | 3400 |
| 49 | 6300 |
| 50 | 403 |

The following abbreviations are used throughout the text:

| | |
|---|---|
| Me: | methyl |
| Et: | ethyl |
| t-Bu: | tert-butyl |
| Ar: | aryl |
| Ph: | phenyl |
| Bn: | benzyl |
| DCE: | dichloroethylene |
| DCM: | dichloromethane |
| DMF: | N,N-dimethylformamide |
| LDA: | lithium diisopropylamide |
| BOC: | t-butyloxycarbonyl |
| HMDS: | hexamethyldisilazane |
| THF: | tetrahydrofuran |
| Ac: | acetyl |
| DMSO: | dimethylsulfoxide |
| DMEM: | Dulbecco's Modified Eagle Medium (High Glucose) |
| FBS: | fetal bovine serum |
| rt: | room temperature |
| aq: | aqueous |
| HPLC: | high performance liquid chromatography |
| MS: | mass spectrometry |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

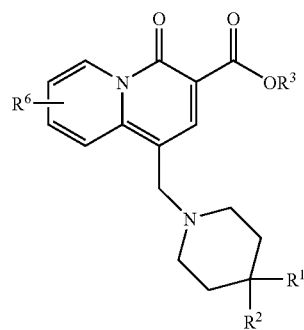

wherein
$R^1$ is selected from the group consisting of
  (1) cyano,
  (2) —C(=O)—$OR^{4A}$,
  (3) —C(=O)—$R^{4A}$,
  (4) —OH, and
  (5) phenyl;
$R^2$ is selected from the group consisting of
  (1) —$(CH_2)_n$-aryl, and
  (2) heteroaryl,
    wherein said aryl or heteroaryl moiety is optionally substituted with one or more
    (a) halogen,
    (b) hydroxy,
    (c) —O—$C_{1-6}$ alkyl,
    (d) —$C_{1-6}$ alkyl,
    (e) —$C_{2-6}$ alkenyl
    (f) —$S(O)_m$—$R^{4A}$,
    (g) —$C_{2-6}$ alkynyl, and
    (h) —$N(R^{4A}R^{4B})$;
$R^3$ is selected from the group consisting of
  (1) hydrogen,
  (2) —$C_{1-6}$ alkyl, and
  (3) —$CH_2$-aryl,
    wherein said $R^3$ alkyl or aryl moiety is optionally substituted with one or more
    (a) halogen,
    (b) cyano, and
    (c) —O—$C_{1-6}$ alkyl, wherein said alkyl is optionally substituted with one or more halo;
$R^{4A}$ and $R^{4B}$ are each independently selected from the group consisting of
  (1) hydrogen,
  (2) —$C_{1-6}$ alkyl,
  (3) —$(CH_2)_n$-aryl,
    wherein said $R^{4A}$ or $R^{4B}$ alkyl or aryl moiety is optionally substituted with one or more
    (a) halogen,
    (b) cyano, and
    (c) —O—$C_{1-6}$ alkyl, wherein said alkyl is optionally substituted with one or more halo;
$R^6$ is optionally present at one or more of the ring carbon atoms, and each $R^6$ is independently selected from the group consisting of
  (1) halogen,
  (2) —$C_{1-6}$ alkyl, and
  (3) —$(CH_2)_n$-aryl, wherein said R⁶ alkyl or aryl moiety is optionally substituted with one or more
(a) halogen,
(b) cyano, and
(c) —O—$C_{1-6}$ alkyl, wherein said alkyl is optionally substituted with one or more halo;
m is 0, 1 or 2;
n is 0, 1 or 2;
or a pharmaceutically acceptable salt thereof.

2. A compound of claim 1, wherein R¹ is cyano.

3. A compound of claim 1, wherein R¹ is selected from the group consisting of
(1) —C(=O)—OR$^{4A}$,
(2) —C(=O)—R$^{4A}$,
(3) —OH.

4. A compound of claim 1, wherein R$^{4A}$ and R$^{4B}$ are each independently selected from $C_{1-6}$ alkyl.

5. A compound of claim 1, wherein R² is pyridyl, and the pyridyl group is optionally substituted with one or more
(a) halogen,
(b) hydroxy,
(c) —O—$C_{1-6}$ alkyl
(d) —$C_{1-6}$ alkyl, and
(e) —$C_{2-6}$ alkenyl.

6. A compound of claim 5, wherein the pyridyl is 2-pyridyl.

7. A compound of claim 1, wherein R² is phenyl, optionally substituted with one or more
(a) halogen,
(b) hydroxy,
(c) —O—$C_{1-6}$ alkyl
(d) —$C_{1-6}$ alkyl, or
(e) —$C_{2-6}$ alkenyl.

8. A compound of claim 1, wherein R³ is hydrogen.

9. A compound of claim 1, wherein R⁶ is absent.

10. A compound of claim 1, wherein R⁶ is a halogen present at one ring carbon atom.

11. A compound of claim 1, wherein the compound of formula (I) is a compound of formula (II):

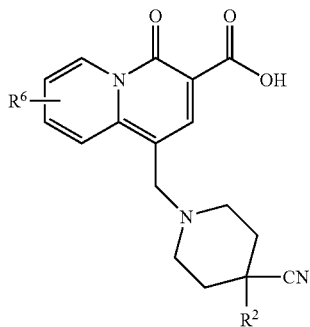

wherein
R² is selected from the group consisting of
(1) —(CH₂)$_n$-aryl, and
(2) heteroaryl,
wherein said aryl or heteroaryl moiety is optionally substituted with one or more
(a) halogen,
(b) hydroxy,
(c) —O—$C_{1-6}$ alkyl
(d) —$C_{1-6}$ alkyl,
(e) —$C_{2-6}$ alkenyl;

R⁶ is optionally present at one or more of the ring carbon atoms, and each R⁶ is independently selected from the group consisting of
(1) halogen,
(2) —$C_{1-6}$ alkyl, and
(3) —(CH₂)$_n$-aryl,
wherein said R⁶ alkyl or aryl moiety is optionally substituted with one or more
(a) halogen,
(b) cyano, and
(c) —O—$C_{1-6}$ alkyl, wherein said alkyl is optionally substituted with one or more halo; and
n is 0, 1 or 2;
or a pharmaceutically acceptable salt thereof.

12. A compound of claim 1, wherein the compound of formula (I) is a compound of formula (III)

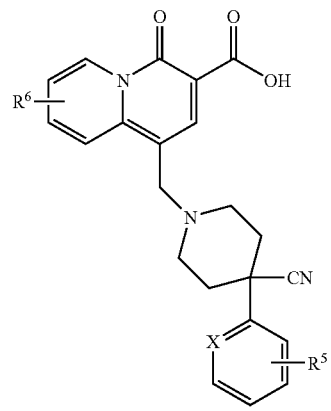

wherein
X is selected from the group consisting of
(1) CH, and
(2) N, and
R⁵ is optionally present and is selected from the group consisting of
(1) halogen,
(2) hydroxy,
(3) —O—$C_{1-6}$ alkyl,
(4) —$C_{1-6}$ alkyl, and
(5) —$C_{2-6}$ alkenyl;
R⁶ is optionally present at one or more of the ring carbon atoms, and each R⁶ is independently selected from the group consisting of
(1) halogen,
(2) —$C_{1-6}$ alkyl, and
(3) —(CH₂)$_n$-aryl,
wherein said R⁶ alkyl or aryl moiety is optionally substituted with one or more
(a) halogen,
(b) cyano, and
(c) —O—$C_{1-6}$ alkyl, wherein said alkyl is optionally substituted with one or more halo; and
or a pharmaceutically acceptable salt thereof.

13. A compound of claim 12, wherein X is N.

14. A compound of claim 1, which is selected from the group consisting of
1-[(4-cyano-4-pyridin-2-ylpiperidin-1-yl)methyl]-4-oxo-4H-quinolizine-3-carboxylic acid;
1-{[4-cyano-4-(4-methylpyridin-2-yl)piperidin-1-yl]methyl}-4-oxo-4H-quinolizine-3-carboxylic acid;

1-{[4-cyano-4-(3-fluorophenyl)piperidin-1-yl]methyl}-4-oxo-4H-quinolizine-3-carboxylic acid;
1-[(4-cyano-4-pyridin-3-ylpiperidin-1-yl)methyl]-4-oxo-4H-quinolizine-3-carboxylic acid;
1-{[4-(3-bromopyridin-2-yl)-4-cyanopiperidin-1-yl]methyl}-4-oxo-4H-quinolizine-3-carboxylic acid;
1-{[4-cyano-4-(3-vinylpyridin-2-yl)piperidin-1-yl]methyl}-4-oxo-4H-quinolizine-3-carboxylic acid;
1-{[4-cyano-4-(5-vinylpyridin-2-yl)piperidine-1-yl]methyl}-4-oxo-4H-quinolizine-3-carboxylic acid; and
Sodium 1-[(4-cyano-4-pyridin-2-ylpiperidin-1-yl)methyl]-9-methyl-4-oxo-4H-quinolizine-3-carboxylate;
or a pharmaceutically acceptable salt thereof.

15. A compound of claim 1, wherein $R^3$ is hydrogen, and $R^1$ and $R^2$ are defined as follows:

| $R^2$ | $R^1$ |
|---|---|
| 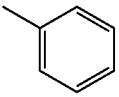 | CN |
| 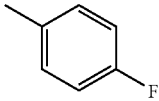 | CN |
| 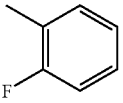 | CN |
| 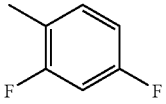 | CN |
| 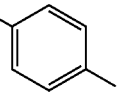 | CN |
| 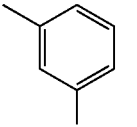 | CN |
| 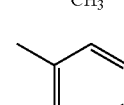 | CN |
| 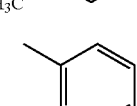 | CN |
| 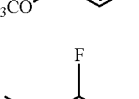 | CN |

-continued

| $R^2$ | $R^1$ |
|---|---|
| 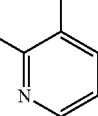 | CN |
| 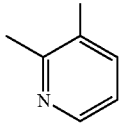 | CN |
| 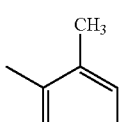 | CN |
| 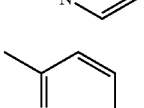 | CN |
| 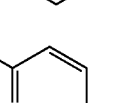 | CN |
| 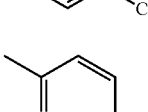 | CN |
| 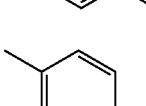 | CN |
| 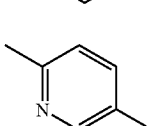 | CN |
| 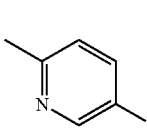 | CN |
| 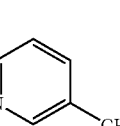 | CN |
| 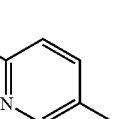 | CN |
| 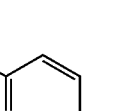 | CN |
| 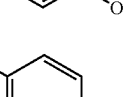 | CN |

-continued
| R² | R¹ |
|---|---|
| 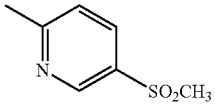 | CN |
| 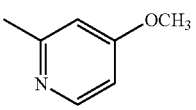 | CN |
| 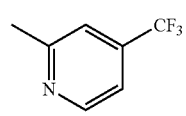 | CN |
| 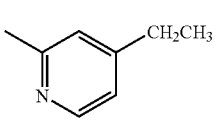 | CN |
| 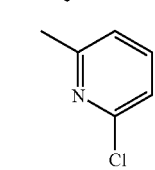 | CN |
| 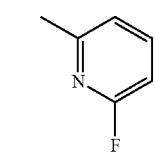 | CN |
| 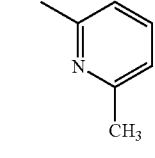 | CN |
| 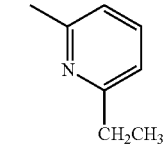 | CN |
| 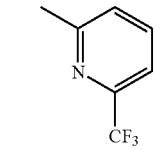 | CN |
| 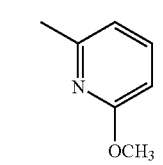 | CN |
| 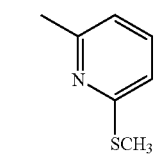 | CN |
-continued
| R² | R¹ |
|---|---|
| 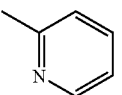 | CN |
| 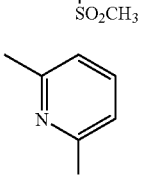 | CN |
| 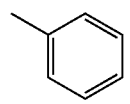 | COCH₃ |
| 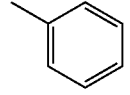 | 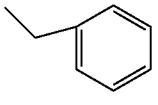 |
| 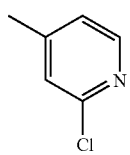 | CO₂CH₂CH₃ |
| 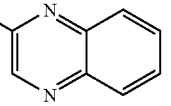 | OH |
| 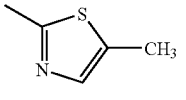 | CN |
| 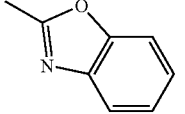 | CN |
| 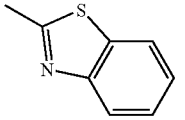 | CN |
or a pharmaceutically acceptable salt thereof.
16. A pharmaceutical composition comprising a therapeutically effective amount of a compound of claim 1, or a pharmaceutically acceptable salt thereof, and a pharmaceutically acceptable carrier.
\* \* \* \* \*